(12) United States Patent
Müller et al.

(10) Patent No.: US 7,790,108 B2
(45) Date of Patent: Sep. 7, 2010

(54) REAGENT CARTRIDGE WITH A REAGENT CONTAINER FOR A PARTICLE-CHARGED REAGENT, FOR NON-INVASIVE HOMOGENIZATION OF THE LATTER

(75) Inventors: Hans-Jürgen Müller, Bernried (DE); Bernd Drescher, Tutzing (DE); Karl-Heinz Mann, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1062 days.

(21) Appl. No.: 11/021,071

(22) Filed: Dec. 22, 2004

(65) Prior Publication Data
US 2005/0153426 A1 Jul. 14, 2005

(51) Int. Cl.
*G01N 33/00* (2006.01)
(52) U.S. Cl. .......................... 422/68.1; 422/72; 422/99; 422/100; 422/101; 422/102; 422/104
(58) Field of Classification Search ................ 422/68.1, 422/72, 99, 100, 101, 102, 104
See application file for complete search history.

(56) References Cited

U.S. PATENT DOCUMENTS

| | | | |
|---|---|---|---|
| 2,413,094 A | * | 12/1946 | Yost ........................... 366/227 |
| 3,443,909 A | * | 5/1969 | Goossens ..................... 422/108 |
| 5,183,638 A | | 2/1993 | Wakatake |
| 5,578,272 A | | 11/1996 | Koch et al. |
| 5,580,524 A | | 12/1996 | Forrest et al. |
| 5,637,962 A | | 6/1997 | Prono et al. |
| 5,658,799 A | | 8/1997 | Choperena et al. |
| 5,788,928 A | | 8/1998 | Carey et al. |
| 5,795,784 A | | 8/1998 | Arnquist et al. |
| 5,856,194 A | | 1/1999 | Arnquist et al. |
| 5,985,672 A | | 11/1999 | Kegelman et al. |
| 6,149,872 A | | 11/2000 | Mack et al. |

FOREIGN PATENT DOCUMENTS

| | | |
|---|---|---|
| AU | 7741894 | 5/1995 |
| EP | 0 580 483 | 4/1995 |
| EP | 0 745 855 | 12/1996 |
| EP | 0 757 253 | 2/1997 |
| EP | 0 435 481 | 8/1997 |

* cited by examiner

*Primary Examiner*—Sam P Siefke
(74) *Attorney, Agent, or Firm*—McDonnell Boehnen Hulbert & Berghoff LLP

(57) ABSTRACT

The invention relates to a reagent cartridge for receiving containers. These each contain particle-charged reagents and particle-free reagents. The container receiving the particle-charged reagent is received so as to be able to rotate. The reagent cartridge comprises interconnectable cartridge parts which form containers and which, in the interconnected state, ensure that the container receiving the particle-charged reagent is mounted so as to be able to rotate.

11 Claims, 7 Drawing Sheets

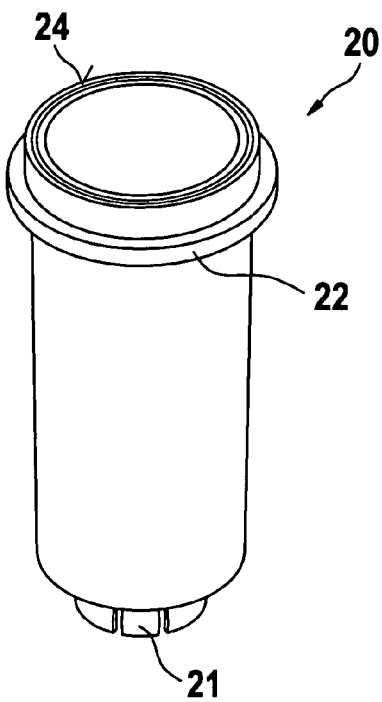
Fig. 4.1
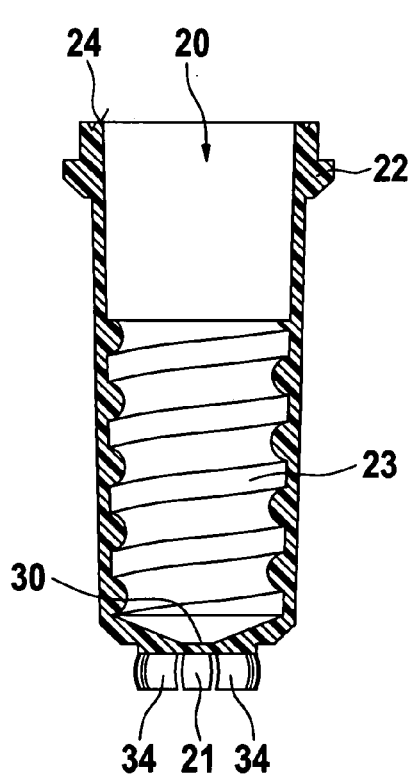
Fig. 4.2
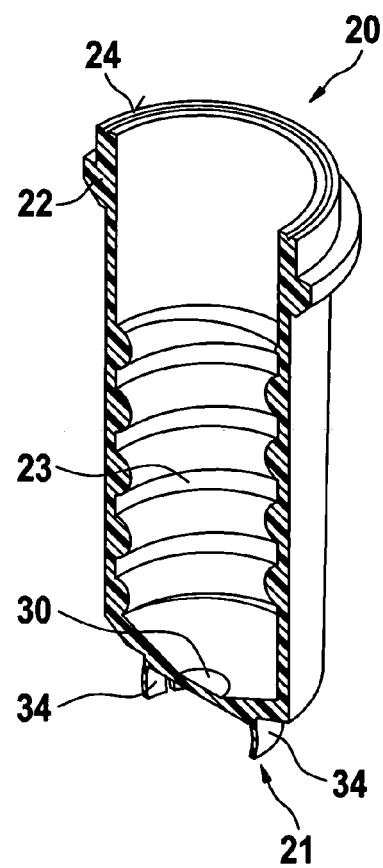
Fig. 4.3

REAGENT CARTRIDGE WITH A REAGENT CONTAINER FOR A PARTICLE-CHARGED REAGENT, FOR NON-INVASIVE HOMOGENIZATION OF THE LATTER

CROSS REFERENCE

This application claims priority to German patent application No. 103 60 526.6 filed Dec. 22, 2003, which is incorporated by reference herein in its entirety.

FIELD OF THE INVENTION

The invention relates to a reagent cartridge with a reagent container for a particle-charged reagent, which reagent cartridge is especially suitable for non-invasive homogenization of coated and sedimenting particles, and also to a magazine.

BACKGROUND

Diagnostic assay systems in many cases involve the use of particles in a liquid to allow reactions to take place. These involve methods for detection of chemical binding reactions, for example in connection with antigens or antibodies. For correct conduct of assays using these systems, it is generally necessary for the particles in the associated containers to have the most homogeneous dispersion possible at the time of removal. A homogeneous particle dispersion avoids, for example, differences in concentration, caused by sedimentation processes, between successive withdrawals from the containers.

In the area of clinical diagnostic analysis systems for homogenization of particles, for example magnet particles, with connected particle-charged reagent containers, the following methods are already known. Rotary paddles are used. Such rotary paddles are known from EP 0 745 855 and from U.S. Pat. No. 6,772,962. Furthermore, use is made of intermittently rotating circular plastic vials which are equipped with radial inner fins, such as are known from U.S. Pat. No. 5,637,962, U.S. Pat. No. 5,795,784 or also from U.S. Pat. No. 5,856,194. In addition, ultrasound methods are known in which a metering needle excited by ultrasound plunges into the liquid and mixes the latter thoroughly. Such solutions can be taken for example from U.S. Pat. No. 5,658,799, EP 0 580 483 or from U.S. Pat. No. 5,985,672. It is also known to immerse a glass ball into a round, eccentrically rotating glass vial in order to force the content of the glass vial into a mixing movement. Such a method is known, for example, from U.S. Pat. No. 5,183,638. The prior art also includes reagent cartridges having a rotatably mounted container which is driven via a friction gear, for example from U.S. Pat. No. 5,580,524 or from EP 0 435 481.

The methods known from the prior art for homogenizing particle-charged reagents, for example in analysis systems using external actuators such as paddles, have a number of disadvantages. Such a method for homogenization of particle-charged reagents constitutes an invasive mixing method. This means that in principle there is a risk of entrainment between different particle-charged reagent containers. To counteract the risk of entrainment in such analysis systems, these systems use special wash stations and wash fluids with which the risk of entrainment is intended to be counteracted. However, this involves a much greater outlay in terms of equipment in such analysis systems. In analysis systems which use external actuators, for example paddles, for homogenization of particle-charged reagents, a plurality of reagent containers can be processed only sequentially. This in turn means long preparation times for an operation, and there are limitations on the configuration of the apparatus cycle, the time for access to other reagent containers, and the apparatus cycle time. Particle-charged reagents homogenized according to these methods show increased foam formation as the volume of liquid decreases, which results in relatively high reagent pressure volumes.

In certain types of particles, invasively operating ultrasound systems lead to inadmissible changes in the particle coating. A similar phenomenon occurs upon invasive addition of auxiliaries, as represented for example by glass balls. In systems in which radial internal fins are used for homogenization of particle-charged reagents, considerable foam formation takes place when certain liquids are mixed together; the liquid also sprays, which is highly unsatisfactory.

In the systems which are known from the prior art according to U.S. Pat. No. 5,788,928 and EP 0 757 253 and use pivotable cartridges, a significantly greater container volume is generally needed, resulting in more space being required for such systems.

In view of the disadvantages of the methods known from the prior art for homogenization of particle-charged reagents, the object of the present invention is to permit homogenization of particle-charged reagents non-invasively by rotation of a container.

According to the invention, this object is achieved by the features of the claimed invention.

The advantages of the solution proposed according to the invention are that the risk of entrainment can be definitively ruled out by the proposed non-invasive homogenization of the particle-charged liquid. No wash stations are needed. Moreover, no wash fluid is needed, and, finally, no liquid waste is obtained which then has to be disposed of in compliance with legal requirements. In addition, an extremely low dead volume can be achieved, as a result of which the reagent can be better utilized, since foam formation, of the kind arising in the methods known from the prior art, is suppressed. The solution proposed according to the invention also permits greater degrees of freedom in system configuration and affords the possibility of parallelization of access in the reagent area since, from several containers containing reagents, access can be made to one container unit. The parallelization further permits considerably shorter processing times for homogenization, compared to sequential processing.

Moreover, the solution proposed according to the invention permits a parallelization of the first homogenization for reagent cartridges; because of possible particle sedimentation, the first homogenization can in fact be especially time-consuming. Before the first homogenization, no liquid level detection is required, because, when mixing by means of vial rotation, the liquid level inside the reagent cartridges does not need to be known. In contrast, this is required in mixing processes using stirrer paddles, since insufficient immersion of the stirrer paddles can lead to foam formation and undesired spraying.

The assemblable cartridge proposed according to the invention also affords the advantage that lid opening and lid closure operations are no longer needed in the homogenization. The reagent cartridge proposed according to the invention and receiving several reagents is provided with a film closure which avoids extra cycles, such as opening and closing, and thus reduces the throughput times.

The assemblable reagent cartridge proposed according to the invention further represents a cost-effective plastic component which can be mass-produced and permits straightforward cartridge assembly. Thus, a cartridge can be assembled by means of two clip parts provided with curvatures being simply fitted together so as to enclose a container holding particle-charged reagents. The connectable clip parts have large flat surfaces which considerably facilitate labelling. The individual clip parts and the container receiving the particle-charged liquid can be filled at different times from one another.

BRIEF DESCRIPTION OF THE FIGURES

The invention is explained in more detail below with reference to the drawing, in which:

FIGS. 4.1 to 4.3 show views of a container which receives particle-charged reagents and has a spiral structure.

DETAILED DESCRIPTION OF THE INVENTION

Figure 1:
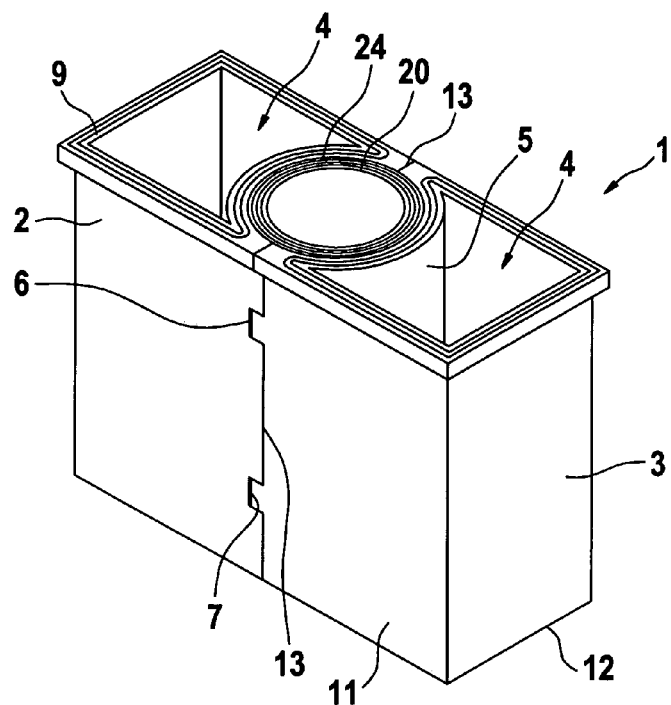
FIG. 1 shows an assembled reagent cartridge comprising two cartridge parts between which a further container is fixed.

The view according to FIG. 1 shows an assembled reagent cartridge according to the present invention still open at the top.

A reagent cartridge 1 is formed by a first cartridge part 2 forming a container, and a second cartridge part 3 also forming a container. The cartridge parts 2, 3 forming containers are each provided with a curvature 5 on their sides facing one another. Situated between the curvatures 5 of the cartridge parts 2, 3, there is a container 20 (beaded vial). The container 20 has, at its top, an annular surface 24 designed as a weld face, just as the cartridge parts 2,3 forming the containers have a weld face 9 at their top. The container 20 is used to receive a particle-charged reagent, while liquid-type reagents are filled into the hollow cavities 4 of the cartridge parts 2, 3 forming containers. At their tops 9, 24 serving as weld faces, the cartridge parts 2, 3 and the container 20 designed as beaded vial can be welded to a film in order to prevent contamination of the content of the container 20 and the cartridge parts 2, 3 forming containers.

As will be seen from the view according to FIG. 1, the cartridge parts 2, 3 forming the containers bear against one another along a butt joint 13. The cartridge parts 2, 3 forming the containers are joined together at the butt joint 13 via catch openings 6 into which catch lugs 7 engage. The reagent cartridge 1 shown in the assembled state in FIG. 1 comprises a large side wall 11 and a front wall 12 which afford large flat surfaces for applying labels. The cartridge parts 2, 3 forming the containers are preferably produced as injection-moulded components on which the catch lugs 7 and the catch openings 9 and the curvatures 5 can be formed on the respective cartridge parts 2, 3 in one operation.

Figure 2:
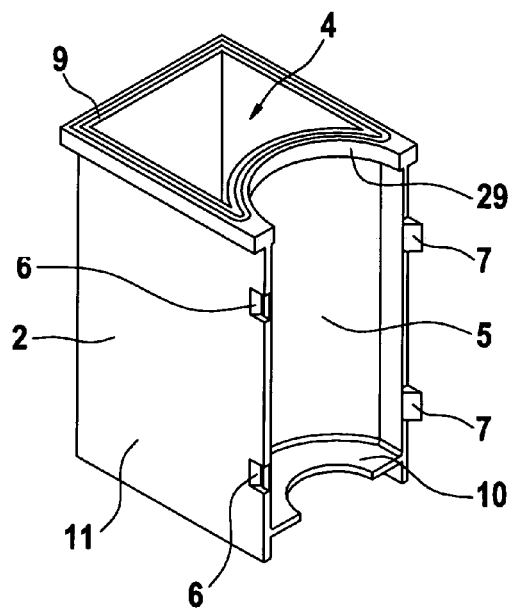
FIG. 2 shows one of the two clip parts of the reagent cartridge in a perspective view.

The view according to FIG. 2 shows one of the two interconnectable cartridge parts of the reagent cartridge.

The view according to FIG. 2 shows that the cartridge part 2 forming one container has, on the side of the curvature 5, a semicircular shoulder 29 and a positioning aid 10. The positioning aid 10 is of semicircular shape in the view according to FIG. 2. The catch lugs 6 are located in the area of the side wall 11, while the catch lugs 7 are formed on the opposite side wall. A weld face 9 is formed at the top of the cartridge part 2 forming a container and surrounds the hollow cavity 4 of said cartridge part 2.

Figure 3:
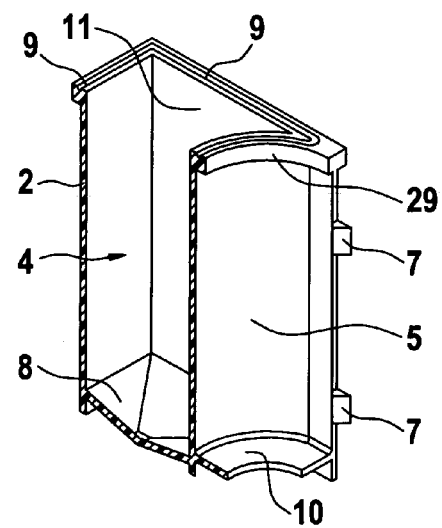
FIG. 3 shows the clip part of the reagent cartridge according to FIG. 2 in half section.

The cartridge part forming a container and shown in FIG. 2 is represented in section in the view according to FIG. 3.

From the view according to FIG. 3 it will be seen that the hollow cavity 4 of the cartridge part 2 forming one container is delimited by a base 8 of the hollow cavity, which base 8 is optimized in terms of dead volume. In the present context, dead volume is to be understood as the reagent volume that can no longer be removed from the hollow cavity 4 of the cartridge part 2.

The weld face 9 at the top of the cartridge part 2 forming a container is designed for a double seal, i.e. the weld face 9 can have a stepped configuration so that it is possible to weld superposed films for closure (double sealing) of the cavity 4 of the cartridge part 2 forming a container. The shoulder 29 shown as a quarter circle in the view according to FIG. 3, and the positioning aid 10 also shown as a quarter circle, serve for rotatable mounting of a container 20 (not shown in FIG. 3) in which a particle-charged reagent is received. On the rear side wall 11 of the cartridge part 2 forming a container, there are projecting lugs 7 which can be injection-moulded in one operation during the injection-molding process during production of the cartridge part 2 designed as container.

FIG. 4.1 shows a container designed as beaded vial for receiving a particle-charged reagent.

At its top, the container 20 has an annular surface 24 to which a film can be welded so that, after the container 20 has been filled with a particle-charged reagent, its interior is protected against contamination. At the top of the container 20 designed as a beaded vial, there is in particular a positioning ring 22 which interacts with the shoulder 29 arranged on the cartridge parts 2, 3 designed as containers. A slotted plastic ring 21 is injection-moulded onto the base of the container 20. The container 20 (beaded vial) receiving the particle-charged reagent can also be produced inexpensively during the injection-moulding process in one operation.

The container 20 is shown in cross section in the view according to FIG. 4.2.

The positioning ring 22 is located underneath the annular surface formed at the top of the container 20 (beaded vial). In the lower area of the container 20, the latter is provided on its inside with a spiral structure 23 in helix form. The spiral structure 23 representing the helix form generates a vertical flow in the cylindrical wall area of the container 20 and an opposing vertical flow in the centre of the container 20 with intermittent rotation. To compensate for this, a defined flow extending in the radial direction is established at the base of the vial, this flow being highly suitable for resuspension of the particles sedimented in the base area of the container 20. The shallow angle of the spiral-shaped structure 23, relative to the surface of the liquid, permits creation of a gentle flow without cavitation phenomena and definitively avoids foam formation in the inside of the container 20 and avoids damage to the particles, which can optionally be provided with a coating.

The container 20 is delimited by a base 30 of the vial. Below the base of the vial, a slotted ring 21 is injection-moulded onto the container 20 (beaded vial). The slotted ring comprises tabs 34 which are separated from one another by slits, are resilient and permit a coupling connection to a coupling piece 31 (not shown in FIG. 4.2).

The perspective view in FIG. 4.3 shows that the spiral structure 23 extends in a helix form along the two lower thirds of the container 20 (beaded vial). The base 30 of the vial is of fructoconical design. Below the base 30 of the vial, there is a slotted ring 21 which is injection-moulded onto the container 20, for receiving a particle-charged reagent, and whose tabs 34 individually separated by slits are of a resilient design so as to permit simple coupling to a coupling piece on a magazine.

Figure 5:
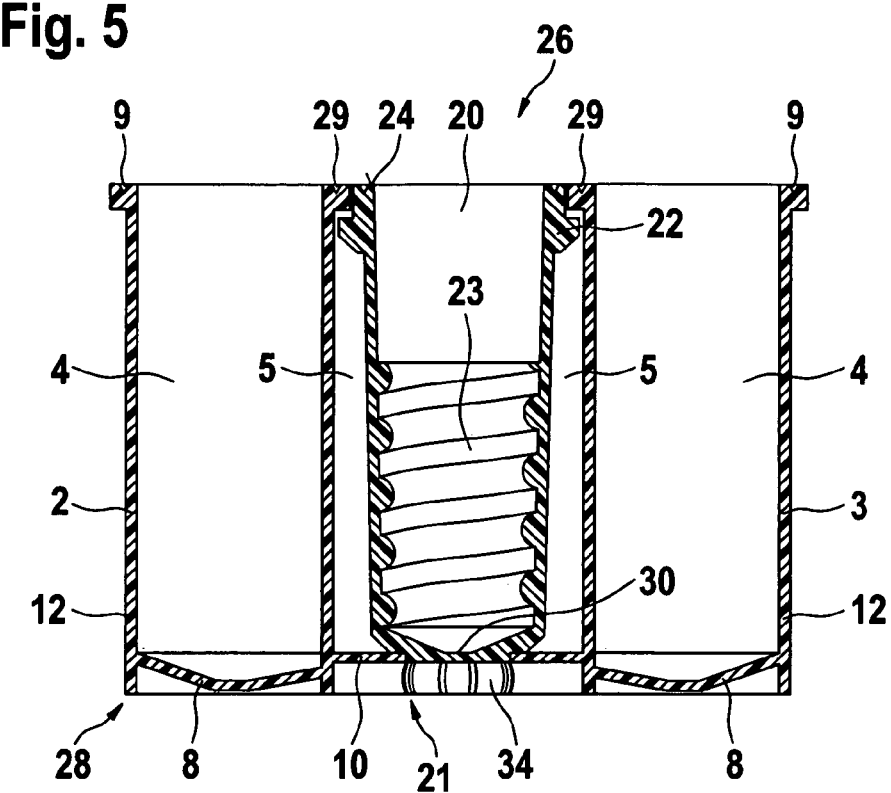
FIG. 5 shows an assembled reagent cartridge between whose clip parts the container according to FIGS. 4.1 to 4.3 is fixed.

FIG. 5 shows an assembled reagent cartridge, two cartridge parts forming containers, and, received between these, a container 20 receiving a particle-charged reagent.

The view according to FIG. 5 shows that the container 20 receiving the particle-charged reagent is mounted rotatably between the cartridge parts 2 and 3 forming the containers. The container 20 (beaded vial) is on the one hand fixed by the semicircular positioning aids 10 of the cartridge parts 2,3 serving as containers above the slotted ring 21, and, on the other hand, by the semicircular shoulders 29 bearing above the positioning ring 22. In the view according to FIG. 5, a container 20 designed as a beaded vial is mounted between the cartridge parts 2, 3 forming the containers. The container 20 shown in FIG. 5 comprises a spiral structure in helix form 23 which extends above the base 30 of the vial. From the reagent cartridge 1 shown in the assembled state 26 in FIG. 5, it is clear that in the assembled state the reagent cartridge 3 has containers separated from one another. These are the hollow cavities 4 of the cartridge part 2 and of the cartridge part 3 and the hollow cavity of the container 20 for receiving the particle-charged reagent. The hollow cavities 4 of the cartridge parts 2 and 3 and the hollow cavity of the container 20 are in each case delimited by a dead-volume-optimized base 8 and by a frustoconical base 30.

It is clear from the view according to FIG. 5 that both the cartridge part 2 forming a container and the cartridge part 3 forming a container each have a stand surface. The slotted ring 21 formed on the container 20 for receiving the particle-charged reagent also represents a flat stand surface. In the assembled state 26, the stand surfaces of the cartridge parts 2, 3 and of the container 20 for receiving the particle-charged reagent form a flat underside 28 of the reagent cartridge 1 in the assembled state 26. In the assembled state 26, surfaces 9 serving as weld faces are formed on the top of the reagent cartridge 1; the annular surface 24 also serving as a weld face is located on the top of the container 20 for receiving the particle-charged reagent.

From the view according to FIG. 5, it will further be seen that the slotted ring 21 has a number of resilient tabs 34 separated from one another by slits. Reference number 5 indicates the curved surfaces of the cartridge parts 2,3 forming containers, these curved surfaces forming a hollow cavity between the positioning aids 10 and the positioning ring 22 when the cartridge parts 2,3 forming containers are interconnected, i.e. joined together.

Figure 6:
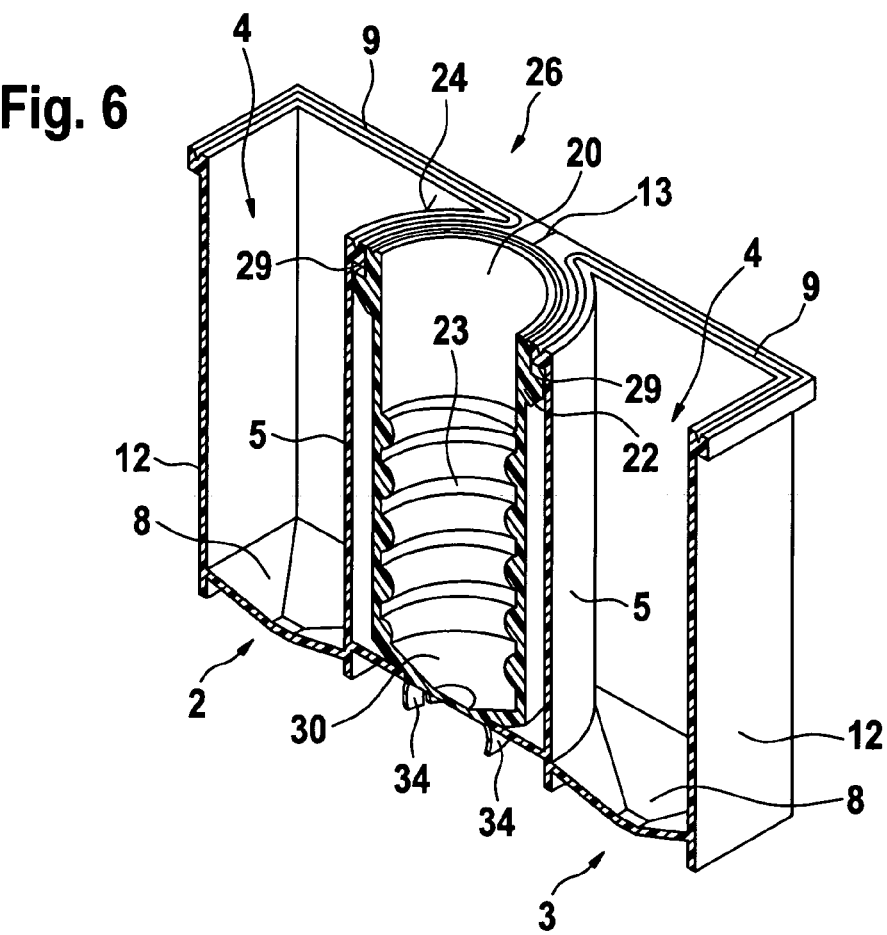
FIG. 6 shows a cross section through the assembled reagent cartridge according to the view in FIG. 5.

FIG. 6 shows a cross-sectional view of the assembled reagent cartridge shown in FIG. 5.

The container 20 used for receiving a particle-charged reagent 20 and mounted rotatably between the cartridge parts 2, 3 forming containers is held in the upper area by the shoulders 29 and the positioning ring 22 injection-moulded onto the container 20, whereas the rotatable mounting of the container 20 (beaded vial) in the lower area is effected by the semicircular positioning aids 10 which are injection-moulded on the underside of the curved surfaces 5 of the cartridge parts 2, 3. Each of the cartridge parts 2, 3 forming containers comprises a dead-volume-optimized base 8 (cf. view according to FIG. 3).

In the view according to FIG. 6, between the cartridge parts 2, 3 forming containers, a container 20 is introduced which has a spiral structure 23 in helix form on its inside. Upon rotation of the container 20 via the ring 21 with tabs 34, the spiral structure 23 in helix form on the inside of the container 20 effects homogenization of the particle-charged reagent in the container 20 (beaded vial), as a result of which differences in concentration caused by sedimentation can be compensated for, i.e. a uniform particle dispersion of the particle-charged reagent can be achieved.

The front walls 12 of the reagent cartridge 1 in the assembled state 26 can be used for application of labels. The same applies for the side wall 11 of the reagent cartridge 1 lying between the front walls 12 in the assembled state 26. Along the butt joint 13, the cartridge parts 2, 3 forming containers bear against one another; for reasons of clarity of the drawings, the interacting catch openings 6 and lugs 7 along the butt joint 13 are not shown in FIGS. 5 and 6.

Figure 7:
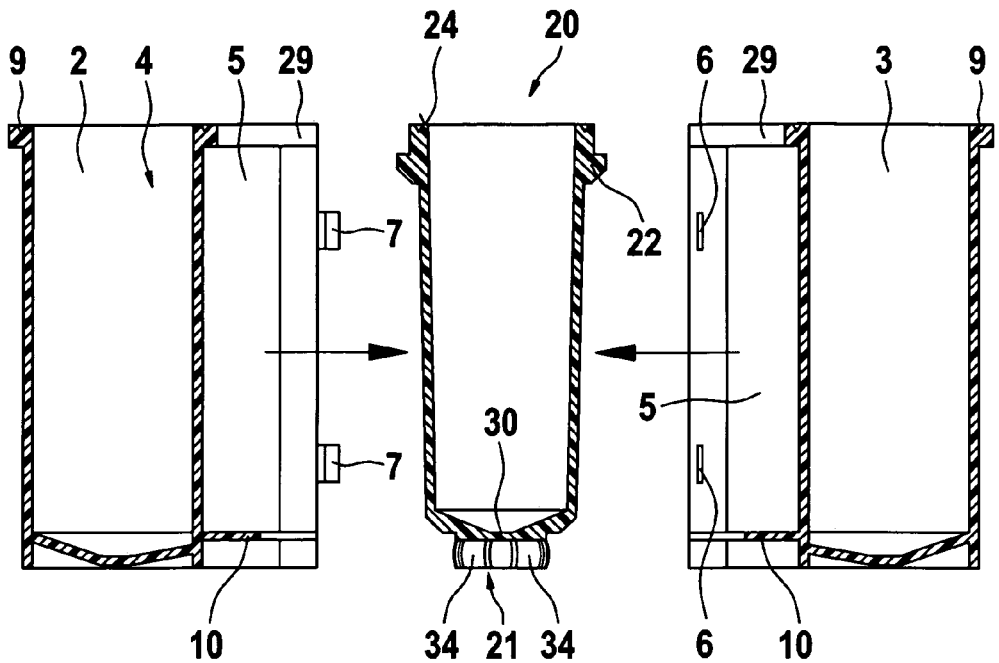
FIG. 7 shows the individual parts from which the reagent cartridge according to the invention is assembled.

FIG. 7 shows the individual containers from which the reagent cartridge according to the invention is assembled.

The cartridge parts 2, 3 and the container 20 each shown in cross section are joined to one another in the direction of the arrows. Upon assembly of the cartridges 2, 3 forming containers, the lugs 7 of one cartridge part 2 forming a container engage in the catch openings 6 of the other cartridge part 3 forming a container. During assembly, the container 20 (beaded vial) for receiving a particle-charged reagent is oriented between the assembled cartridge parts 2, 3 in such a way that the positioning ring 22 comes to bear under the shoulders 29 at the top of the two cartridge parts 2. The two positioning aids 10 arranged at the lower area of the cartridge parts 2, 3 forming containers enclose the container 20 above the slotted ring 21 which has resilient tabs 34. This permits a rotatable mounting of the container 20 (beaded vial) receiving a particle-charged reagent in a reagent cartridge shown in FIG. 8 in the assembled state 26. By virtue of the design of the stand surface of the cartridge part 2 forming a container and of the other cartridge part 3 forming a container and the geometry of the slotted ring 21, a flat underside 28 is obtained in the assembled state 26 of the reagent cartridge 1. By virtue of the fact that the individual containers can be joined together, i.e. the cartridge parts 2 and 3 and the container 20 (beaded vial), reagents can be introduced and cartridges assembled in a temporally independent manner. As can be seen from FIGS. 7 and 8, the reagent cartridge 1 proposed according to the invention is assembled by simply fitting the components 2, 3 and 20 together, without additional parts such as a lid or neck-shaped connector element being needed.

Figure 9:
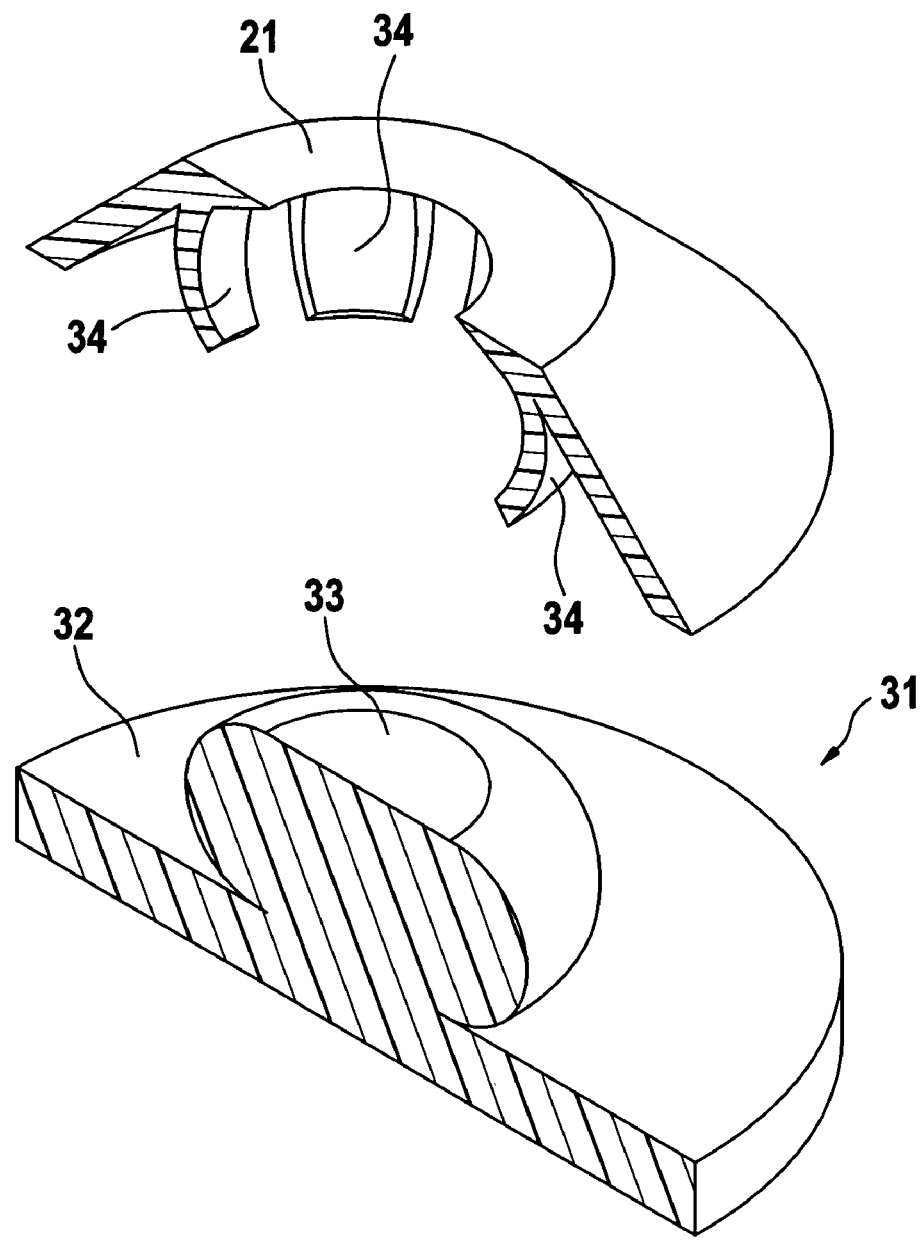
FIG. 9 shows an attachment piece via which a container integrated in the reagent cartridge and receiving a particle-charged liquid can be set in rotation.

The view according to FIG. 9 shows a coupling piece with which the slotted ring is fitted on the underside of the container receiving the particle-charged reagent.

Figure 8:
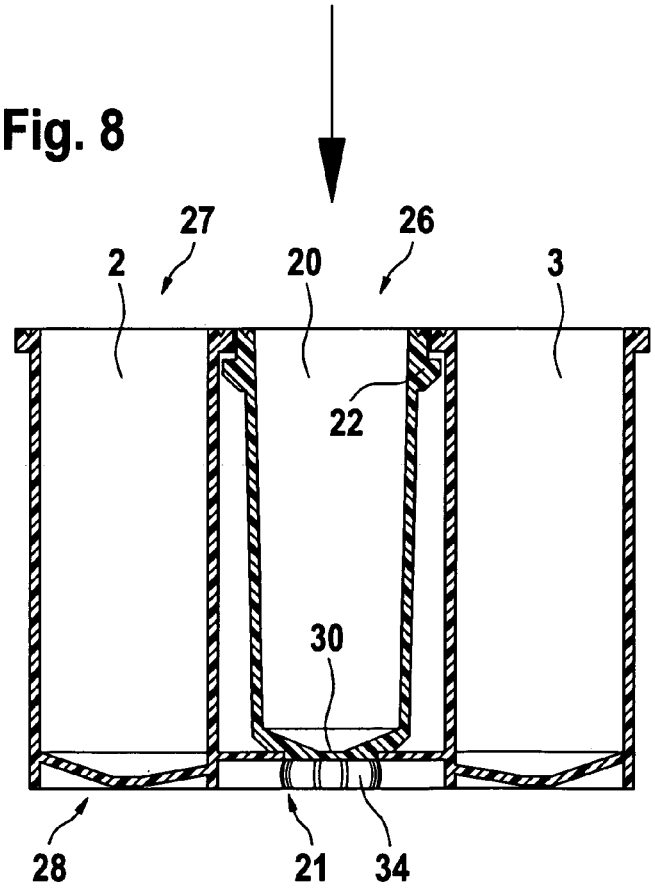
FIG. 8 shows the reagent cartridge assembled from the individual parts according to FIG. 7.

The coupling piece 31 shown in FIG. 9 has a disc-shaped stand 32 and a coupling head 33 formed on the latter. When the reagent cartridge 1 in the assembled state 26 according to FIG. 8 is fitted, the slotted ring, i.e. its resilient tabs 34, engages on the coupling head 33. The resilient tabs 34 separated from one another by slits completely surround the coupling head 33. By means of the slotted ring 21 formed on the container 20 to be set in rotation for receiving a particle-charged reagent, and the coupling piece 31, a coupling connection is established through which a rotation can be introduced into the container 20 (beaded vial) receiving the particle-charged reagent. The locking engagement of the tabs 34 of the slotted ring 21 assists further in the correct positioning of the container 20 inside the reagent cartridge 1 and is advantageous for low-friction vial rotation inside the reagent cartridge 1 in the assembled state 26. The engagement of the slotted ring 21 on the coupling piece 31 is effected by manual or automatic attachment of a reagent magazine, as will be described below.

For the sake of completeness, it should be noted that the catch connection shown by way of example in FIG. 7 between the catch openings 6 and the lugs 7 on the interconnectable cartridge parts 2, 3 forming containers is also configured in such a way that the two cartridge parts cannot be detached from one another without damage.

Figure 10:
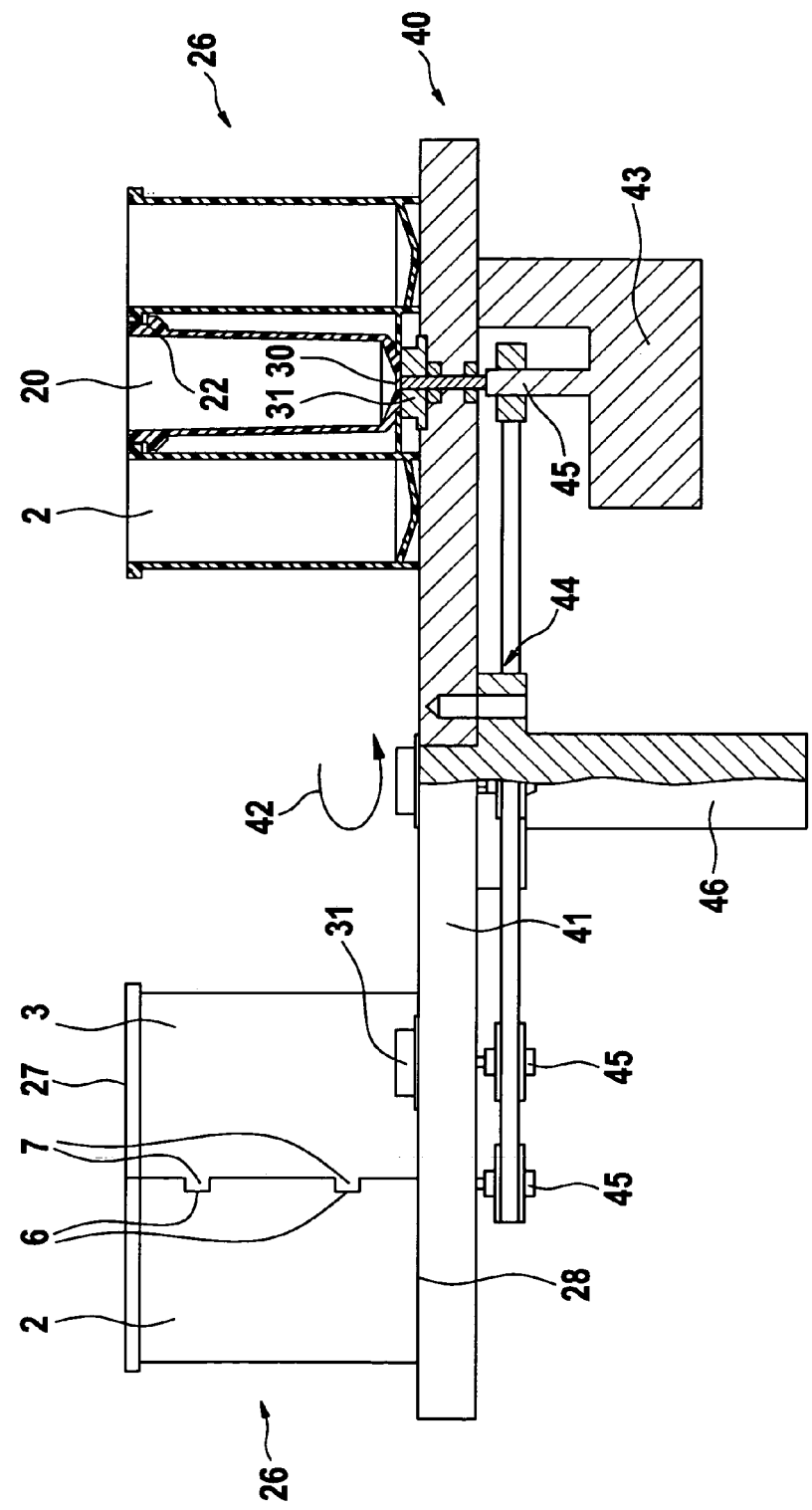
FIG. 10 shows a mixing magazine with a magazine plate on whose top face the reagent cartridges proposed according to the invention are received.

The view in FIG. 10 shows a diagrammatic representation of a reagent magazine.

The reagent magazine 40 comprises in principle a magazine plate 41 supported by a central shaft 46. The magazine plate 41 rotates in the direction of rotation 42, indicated by the arrow identified by reference label 42. Instead of the magazine plate 41 shown in FIG. 10 which represents a possible alternative embodiment, the reagent magazine 40 can also be configured in a matrix arrangement. A plurality of coupling pieces 31 are let into the magazine plate 41. The coupling pieces 31 are for their part driven by a drive shaft 45 which communicates with a drive mechanism 43 via a gear 44. Reagent cartridges 1 in the assembled state 26 are positioned on the top of the magazine plate 41. By virtue of the flat underside 28 of the reagent cartridges 1 in the assembled state 26, these stand flat on the top of the magazine plate 41. The reagent cartridges 1 in the assembled state 26 are positioned on the top of the magazine plate 41 in such a way that the slotted ring of a container 20 of a reagent cartridge 1 in the assembled state 26 engages round the driven coupling pieces 31 on the magazine plate 41. In this way, a first coupling connection is established between the container 20 mounted in the reagent cartridge 1 in the assembled state 26 for receiving a particle-charged reagent. By means of the drive mechanism 43, the gear 44 and the drive shaft 45 of the coupling piece 31, the container 20 mounted rotatably in the reagent cartridge 1 for receiving a particle-charged reagent is set in rotation, while the reagent cartridge 1 in the assembled state 26 remains in its position at the top of the magazine plate 41. In this way, a reagent cartridge 1 can be used to receive three reagents, of which the reagent to be homogenized, because it contains sedimenting particles, is held in the container 20 (beaded vial) driven via the coupling connection 21, 31. Accordingly, several reagents can be prepared for further processing in one operation per reagent cartridge 1. From the view according to FIG. 10, it is clear that a plurality of reagent cartridges 1 corresponding to the number of driven coupling pieces 31 can be treated in parallel on the top of the magazine plate 41. The cartridge parts 2, 3 forming containers are each releasably connected to one another via the catches 6, 7, catch openings 6 and catch lugs 7, and the clip connection between the cartridge parts 2, 3 forming the containers can also be configured such that straightforward detachment is no longer possible.

Figure 11:
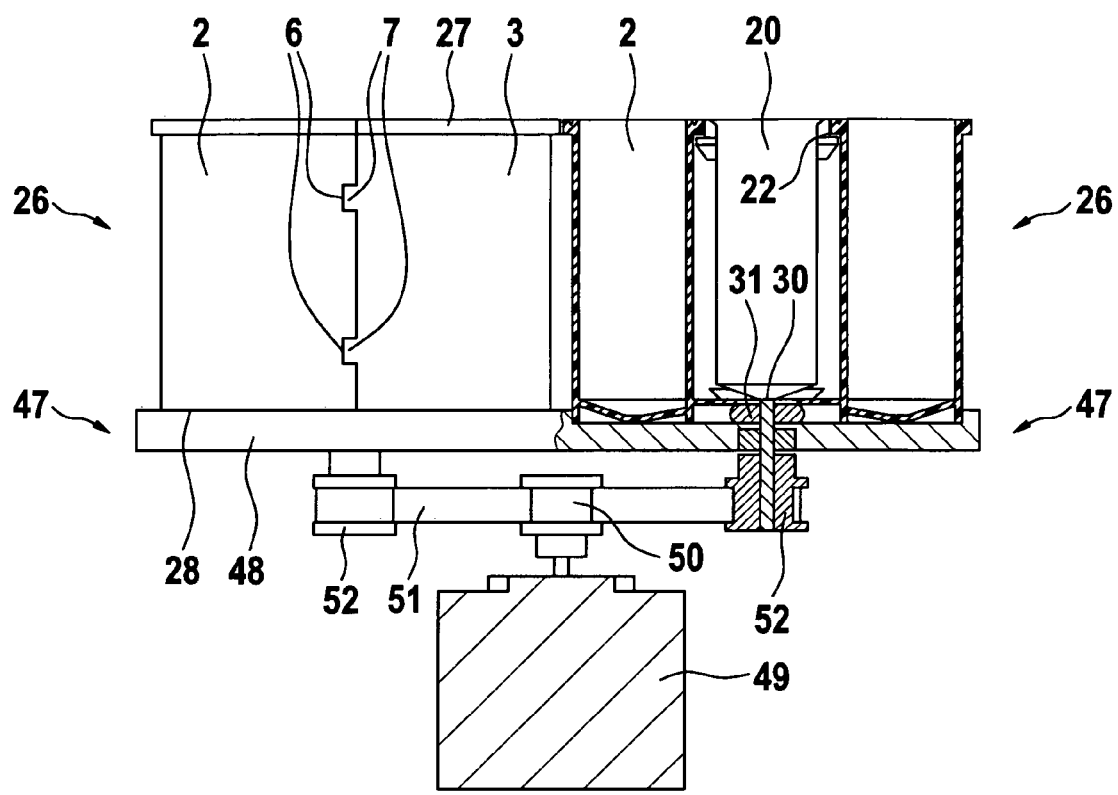
FIG. 11 shows a perspective view of the device according to FIG. 10, in partial cross section.

The view in FIG. 11 shows, in a diagrammatic representation, a reagent magazine in matrix arrangement.

The view according to FIG. 11 shows reagent cartridges which include cartridge part 2 (R1 vial) forming the first container and cartridge part 3 forming the second container. The cartridge parts 2 and 3 are connected to one another by a catch connection, provided by the catch opening 6 and by the lug 7 engaging in the latter. The two reagent cartridges received in FIG. 11 in a reagent magazine 47 in matrix arrangement stand with their flat undersides 28 on a plate 48 of the reagent magazine 47. The reagent cartridges are closed at their tops and contain individual containers 20 (beaded vials). The beaded vials 20 are secured with the aid of positioning rings 22 and coupled to the coupling piece 31 in the area of their flange base 30. The coupling piece 31 is in turn driven by a drive shaft 52 which is provided with a belt wheel or the like and can be driven, for example, by a toothed belt 51. The toothed belt 51 surrounds a further drive wheel which is arranged on the reagent cartridge shown on the left-hand side of FIG. 11 consisting of the cartridge part 2 forming first container and cartridge part 3 forming second container. The toothed belt 51 is driven via a toothed wheel 50 of a drive mechanism 49 and sets in rotation by means of drive shafts 52, of the coupling pieces 31, the containers 20 (beaded vials) coupled to the underside in the area of the vial base 30 by the coupling piece 31 inside the reagent cartridges.

With the embodiment variants shown in FIG. 11, three reagents can be received in different containers 20 (beaded vials) in one reagent cartridge, of which the middle reagent-containing container vial 20 to be homogenized can be set in rotation via the coupling piece 31, the drive shaft 52, the toothed belt 51 and the drive mechanism 49. In this way, as in the embodiment variant shown in FIG. 10, several reagents can be made ready for further processing per reagent cartridge 1 in one operation. The reagent to be homogenized, since it contains sedimenting particles, is preferably received in the container 20 (beaded vial) driven via the coupling connection 31, 52. According to the size of the plate surface of the plate 48 for the reagent magazine 47 in matrix arrangement and according to the number of the drive shafts 52 driven via the toothed belt 51, a multiplicity of reagent cartridges 1 can be treated in matrix arrangement in the reagent magazine 47 shown in FIG. 11.

LIST OF REFERENCE NUMBERS 1 reagent cartridge
2 first cartridge part forming a container (R1 vial)
3 second cartridge part forming a container (R2 vial)
4 hollow cavity
5 curved side
6 catch opening
7 catch lug
8 base of hollow cavity
9 weld face
10 positioning aid
11 side wall
12 front wall
13 butt joint
20 container (beaded vial)
21 slotted ring
22 positioning ring
23 spiral-shaped structure (helix form)
24 annular surface (stepped weld face)
26 assembled reagent cartridge
27 top of reagent cartridge
28 flat underside of reagent cartridge
29 shoulder
30 base of vial
31 coupling piece
32 stand
33 coupling head
34 resilient tabs of slotted ring 21
40 reagent magazine
41 magazine plate
42 direction of rotation 43 drive mechanism
44 gear
45 drive shaft for coupling piece
46 central shaft
47 reagent magazine in matrix arrangement
48 plate in matrix arrangement
49 drive mechanism
50 toothed wheel of drive mechanism
51 toothed belt
52 drive shaft

We claim:

1. A reagent cartridge comprising a rotatable container; interconnectable cartridge parts which form a first container and a second container separated from one another such that their contents do not mix and wherein the cartridge parts, the first container, and the second container upon interconnection with each other form a compartment into which said rotatable container is mounted, wherein the rotatable container is provided on its inside with a spiral-shaped structure in helix form.

2. The cartridge according to claim 1, characterized in that the rotatable container is designed as a beaded vial.

3. The cartridge according to claim 1, characterized in that the cartridge parts forming the containers can be locked together by means of a catch closure.

4. The cartridge according to claim 1, characterized in that the cartridge parts forming the containers have a weld face on their top.

5. The cartridge according to claim 4, characterized in that the cartridge parts forming the containers have a shoulder on their top and have a positioning aid in the area of their flat underside.

6. The cartridge according to claim 1, characterized in that the cartridge parts forming the containers comprise a hollow cavity base with optimized dead volume.

7. The cartridge according to claim 1, characterized in that the cartridge parts forming the containers are provided in each case with a curvature on their sides facing one another.

8. The cartridge according to claim 1, characterized in that the rotatable container is provided at its top with an annular surface designed as a weld face.

9. The cartridge according to claim 1, characterized in that the rotatable container is provided on its underside with a slotted ring which serves as a releasable coupling.

10. The cartridge according to claim 1, characterized in that the rotatable container received rotatably in the cartridge parts forming the containers can be coupled to driven coupling pieces let into a magazine plate.

11. The cartridge according to claim 10, characterized in that the coupling pieces on the magazine plate are driven via drive shafts and gears.

\* \* \* \* \*